United States Patent
Yahiro

(10) Patent No.: US 6,678,391 B2
(45) Date of Patent: Jan. 13, 2004

(54) ORGANISM-SPECIMEN MORPHOLOGICAL-CHANGE DETECTING APPARATUS, AND ORGANISM-SPECIMEN MORPHOLOGICAL-CHANGE DETECTING METHOD

(75) Inventor: Kanji Yahiro, Fukuoka (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/835,489

(22) Filed: Apr. 17, 2001

(65) Prior Publication Data

US 2001/0046689 A1 Nov. 29, 2001

(30) Foreign Application Priority Data

Apr. 18, 2000 (JP) .................................. 2000-116070
May 18, 2000 (JP) .................................. 2000-146554

(51) Int. Cl.⁷ ................................................ G06K 9/00
(52) U.S. Cl. ............................ 382/100; 435/6; 435/41; 435/243
(58) Field of Search ............................ 382/128, 129, 382/130, 131, 132, 133; 435/2, 6, 4, 243, 882, 808, 5, 41, 375, 26; 422/100, 102, 104; 600/407; 436/177; 702/19

(56) References Cited

U.S. PATENT DOCUMENTS

| | | | | |
|---|---|---|---|---|
| 3,635,798 A | * | 1/1972 | Kirkham et al. | ............... 435/2 |
| 3,925,166 A | * | 12/1975 | Blume | ........................ 435/288 |
| 5,134,662 A | * | 7/1992 | Bacus et al. | ................. 382/133 |
| 5,324,633 A | * | 6/1994 | Fodor et al. | ..................... 435/6 |
| 5,357,977 A | * | 10/1994 | Michels | ....................... 600/571 |
| 6,182,719 B1 | | 2/2001 | Yahiro | |
| 6,238,626 B1 | | 5/2001 | Higuchi et al. | |
| 6,296,847 B1 | * | 10/2001 | Gokcen et al. | ............. 424/94.2 |
| 6,299,840 B1 | | 10/2001 | Watanabe et al. | |
| 6,358,470 B1 | | 3/2002 | Higuchi | |

\* cited by examiner

Primary Examiner—Jayanti K. Patel
Assistant Examiner—Abolfazl Tabatabai
(74) Attorney, Agent, or Firm—Wenderoth, Lind & Ponack, L.L.P.

(57) ABSTRACT

The present invention relates to an apparatus of optically detecting morphological change of an organism specimen such as an animal/plant cell. In a candidate compound screening for detecting a candidate compound among compounds, a camera of a microscope apparatus takes images of an organism specimen in a plate before and after a dosage of each compound-containing solution to the organism specimen by a dispensing head. An image processor processes the taken microscopic images and provides numerical data as a quantitative indicator of a state of the organism specimen. The screening apparatus judges whether each compound solved in each solution is the candidate compound by comparing numerical data before and after the dosage of the solution with each other.

18 Claims, 5 Drawing Sheets

FIG. 1A
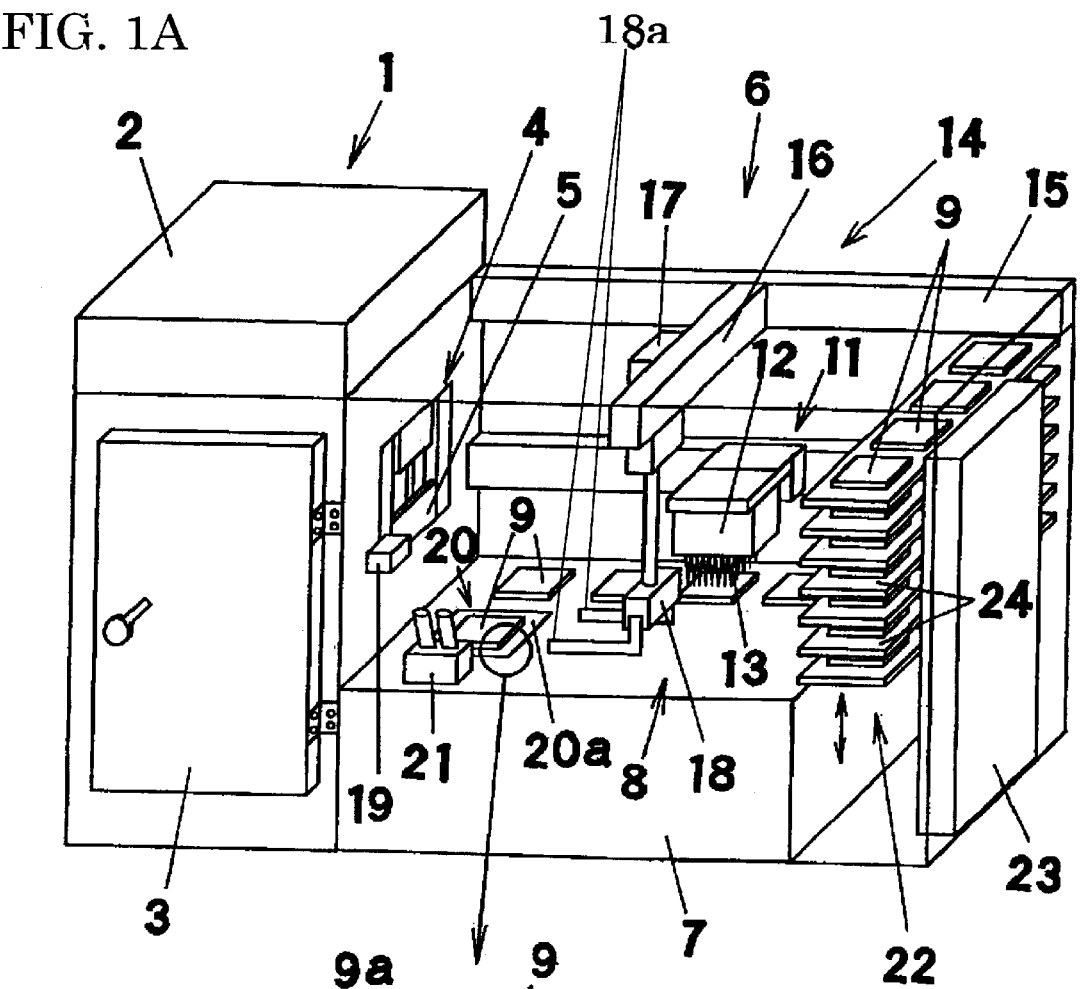
FIG. 1B
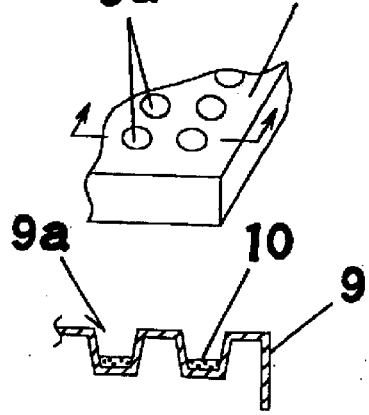
FIG. 1C

ORGANISM-SPECIMEN MORPHOLOGICAL-CHANGE DETECTING APPARATUS, AND ORGANISM-SPECIMEN MORPHOLOGICAL-CHANGE DETECTING METHOD

BACKGROUND OF THE INVENTION

1. Field of the Invention

The present invention relates to an organism-specimen morphological-change detecting apparatus and a method for optically detecting morphological change of an organism specimen such as an animal/plant cell.

2. Description of the Related Art

A new drug development in a drug manufacture industry employs a candidate compound screening for selecting a candidate compound as a candidate of a new valuable medication from various compounds. The candidate compounds are artificially synthesized or sampled from natural products, and a number of their kinds is very large. The candidate compound screening comprises steps of administering a compound-containing solution to be screened to an organism specimen such as an animal/plant cell or a microbe, culturing the organism specimen, and observing change and growth speed of the organism specimen after the dosage. When the organism specimen indicates a distinctive change, the compound solved in the solution is judged as a candidate compound. Therefore, possibility of finding the candidate compound depends on the observation of the change or the growth speed of the organism specimen For observing, for example, sequential changes of a shape, a size, an orientation, and a division state of the cell, and the growth speed of a hypha, work of observation, recording and data-processing of them is required at given time interval. Conventionally, such observation work of the organism specimen entirely relies on a person's operation. An experimental worker visually observes a cell in a view field of a microscope, data-processes required items focusing on an observed part, and records them.

Such observation work is troublesome and expends much effort and time. The work thus decreases efficiency in the entire experiment and applies an excess load on the experimental worker. Data of measurement result intends to vary depending on observation experience and skill of each experimental worker and hardly ensures reliability.

SUMMARY OF THE INVENTION

The present invention addresses the problems discussed above. An organism-specimen morphological-change detecting apparatus in accordance with the present invention comprises a solution administering mechanism for administering a compound-containing solution to an organism specimen, an image taking unit for taking a microscopic image of the organism specimen, and a quantitative evaluation unit for processing the image taken by the image taking unit and outputting numeric data for indicating a state of the organism specimen.

An organism-specimen morphological-change detecting method in accordance with the present invention comprises the following steps:

(a) taking a microscopic images of an organism specimen before a dosage of a compound containing solution;

(b) processing the images taken in step (a), deriving numeric data before the dosage for indicating the state of the organism specimen, and storing the derived numeric data;

(c) taking a microscopic images of the organism specimen at a predetermined interval after the dosage of the solution at the same scaling factor as in step (a); and (d) processing the images taken in step (c), deriving numeric data after the dosage for indicating the state of the organism specimen, and storing the derived numeric data.

BRIEF DESCRIPTION OF THE DRAWINGS

FIG. 1A is a perspective view of a biochemistry material treating apparatus in accordance with an exemplary embodiment of the present invention.

FIG. 1B is a fragmentary perspective view of a plate in accordance with the exemplary embodiment of the present invention.

FIG. 1C is a fragmentary cross sectional view of the plate in accordance with the exemplary embodiment.

DESCRIPTION OF THE PREFERRED EMBODIMENT

Figure 2:
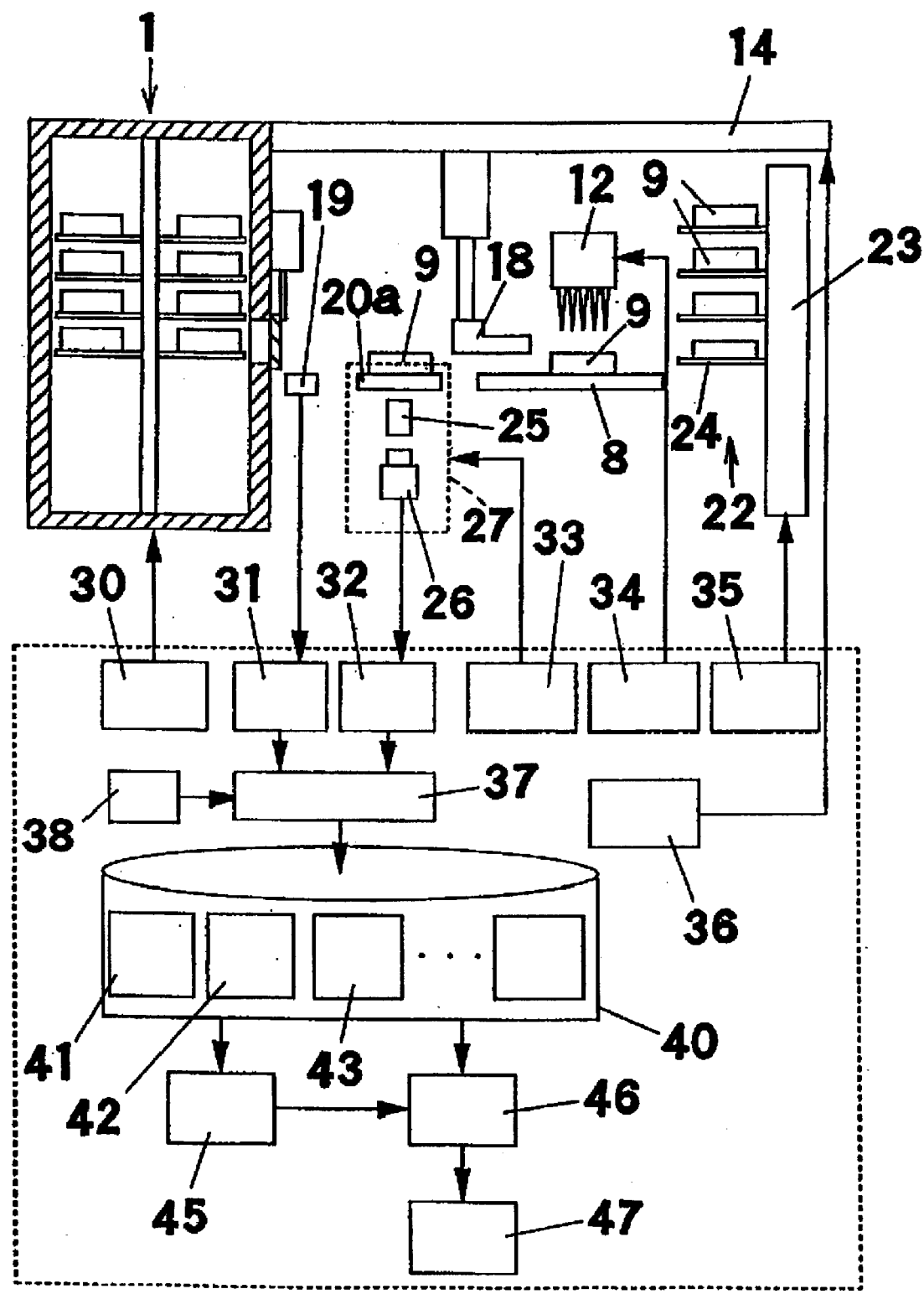
FIG. 2 is a block diagram showing a configuration of the biochemistry material treating apparatus in accordance with the exemplary embodiment.

An embodiment of the present invention will be described hereinafter with reference to the accompanying drawings.

Referring now to FIG. 1A through FIG. 1C, and FIG. 2, a biochemistry material treating apparatus is illustrated. This biochemistry material treating apparatus is used to administer a compound-containing solution to an organism specimen stored in a container, then keeps the container under a predetermined environmental condition, detects morphological change of the organism specimen by observation by a microscope and taking the microscopic images, and judges whether the compound solved in the solution is a candidate compound and selects a candidate compound based on the detection result. The biochemistry material treating apparatus defines a candidate compound screening apparatus.

In FIG. 1A through FIG. 1C, the biochemistry material treating apparatus comprises incubator 1 and dispenser 6. Incubator 1 comprises substantially box-shaped casing 2. Incubator 1 has door 3 in its front surface and pass box 4 for passing a micro titer plate 9 (hereinafter referred to as plate 9) in its side surface. The plate serves as the container storing the organism specimen. Pass box 4 comprises a shutter 5 that is opened as required, for example, when the plate is taken in or out.

Dispenser 6 is disposed adjacent to incubator 1. The upper surface of base 7 of dispenser 6 defines as dispensing stage 8 to which micro titer plates 9 are mounted. As shown in FIG. 1B, each plate 9 include large number of wells 9a for storing liquid specimen containing the organism specimen in a lattice manner. A side surface of each plate 9 has a bar code label (not shown) used for identifying a kind of the plate. A bar code reader reads the bar code to allow automatic identification of each plate 9.

XY table 11 is disposed over dispensing stage 8. XY table 11 is coupled to dispensing head 12 including many dispensing tips 13 (dispensing nozzles). Dispensing head 12 is horizontally moved in dispensing stage 8 by driving XY table 11, and dispenses liquid (e.g. a compound containing solution or liquid specimen containing an organism specimen) between mounted plates 9. Dispensing head 12, in this dispensing operation, sucks the solution from plate 9 storing the solution and delivers the solution to plate 9 storing the organism specimen to allow a dosage of the compound containing solution to the organism specimen. Dispensing head 12 of dispenser 6 thus serves as a solution administering mechanism.

Plate conveying mechanism 14 is disposed over dispensing stage 8. Plate conveying mechanism 14 comprises X-axis table 15, Y-axis table 16, Zθ-axis table 17, and holding head 18. Holding head 18 is coupled to Zθ-axis table 17.

Driving plate conveying mechanism 14 causes two fingers 18a of holding head 18 to clamp plate 9 on dispensing stage 8. Plate conveying mechanism 14 conveys the plate into or out of incubator 1 through pass box 4. Bar code reader 19 disposed on a side surface of pass box 4 reads the bar code on the side surface of conveyed plate 9 in order to identify the plate.

Microscope observation unit 20 is disposed adjacent to pass box 4. Microscope observation unit 20 comprises XY stage 20a disposed on dispensing stage 8 and microscope apparatus 27 (shown in FIG. 2) disposed under XY stage 20a. The organism specimen in plate 9 on XY stage 20a can be observed with the microscope through eye-lens of a lens barrel 21. At this time, as shown in FIG. 2, optical system 25 and camera 26 that are disposed in microscope apparatus 27 can take a microscopic image of the organism specimen.

Microscope observation unit 20 thus serves as an image taking unit for taking the microscopic image of the organism specimen. Plate conveying mechanism 14 is conveying means for conveying plate 9 among dispensing stage 8, microscope observation unit 20, and incubator 1.

Plate storing unit 22 is disposed on a side of dispensing stage 8. Plate storing unit 22 includes many stages of plate mounting shelves 24 on lifter 23 that vertically moves up and down. Each plate mounting shelf 24 stores plates 9. Plate storing unit 22 stores various plates 9 such as plates 9 having various kinds of solutions each of which contains a compound might be a drug candidate or plates 9 having the organism specimen. Holding head 18 takes plates 9 out of plate storing unit 22. Similarly, holding head 18 returns plates 9 after the treatment into plate storing unit 22.

Referring now to FIG. 2, a configuration of a control system is illustrated. Incubator controller 30 controls an operation and an internal environment of incubator 1. Plate identifying unit 31 identifies plate 9 based on a bar code read by bar code reader 19. Image processor 32 processes image data of the organism specimen in plate 9 taken by camera 26 and outputs the state of the organism specimen as numeric data. Number, sizes, distribution, density, and colors of cells as the organism specimen, a size (area) of a cell group (colony), and color information (lightness, chroma, hue) are processed as the numeric data. Lengths, number, thickness, and spreads of tree processes shown in nerve cells are also processed as numeric data. Additionally, shapes and positions of the cells, total luminance in a screen, and spatial frequency are processed as numeric data. These numeric data are used as quantitative indexes for estimating morphological change of the observed organism specimen. Image processor 32 is a quantitative evaluation unit for outputting numeric data for indicating the state of the organism specimen in the microscopic image.

Microscope controller 33 controls microscope apparatus 27 to locate XY stage 20a, set a scaling factor and a focus of optical system 25, and operates taking image with camera 26, during the observation and the image taking of the organism specimen in plate 9 on XY stage 20a. Microscope controller 33 also outputs positional data of XY stage 20a at the time of image taking. The positional data is used to specify a position of measured well 9a. Dispensing head controller 34 controls an operation of dispensing head 12 as well as XY table 11. Lifter controller 35 controls an operation of lifter 23 of plate storing unit 22. Conveying robot controller 36 controls plate conveying mechanism 14 for conveying plate 9 with holding head 18.

Recording processor 37 records the microscopic image and produces data of inspection result, on the basis of the plate identification result by plate identifying unit 31 and the numeric data supplied from image processor 32. In this recording process, the microscopic image, the numeric data supplied from image processor 32, the positional data of XY stage 20a, and timing data counted by clock 38 are linked with an identification number of the plate.

Inspection result storing unit 40 stores inspection result data processed by recording processor 37. Inspection result storing unit 40 has regions 41, 42, 43, . . . for storing a plurality of data, and each storing region receives the inspection result data sequentially in chronological order. In other words, region 41 stores data before a dosage of the solution, and regions 42, 43, . . . sequentially store data at a predetermined interval (every 30 minutes) after the dosage of the solution.

Candidate compound screening unit 45 (morphological change evaluating unit) compares numeric data before and after the dosage of the solution with each other in relation to the organism specimen stored on the same plate, and quantitatively judges change of growth speed and activity of the organism specimen by an action of the compound solved in the solution. Screening unit 45 also discriminates whether the compound solved in the solution is a medication candidate based on the comparison result. Screening unit 45 similarly discriminates a plurality of compound-containing solutions to select a candidate compound from these solutions. Candidate compound screening unit 45 of the present embodiment serves as a morphological change evaluating unit for evaluating the morphological change of the organism specimen. Display processor 46 performs a display process for displaying the selection result of the candidate compound in concert with the inspection result read out from inspection result storing unit 40. Display unit 47 is a monitor, and displays a screen processed by display processor 46.

The numeric data before the dosage of the solution is hitherto compared with the numeric data after the dosage of the solution, and the candidate compound is judged. For some organism specimen, however, a certain numeric data after the dosage of the solution is compared with a subsequent numeric data and a candidate compound is judged.

The configuration of the biochemistry material treating apparatus is structured as discussed above. A method for screening a candidate compound by the biochemistry material treating apparatus will be hereinafter demonstrated. The candidate compound screening comprises steps of taking microscopic images of an organism specimen during its lifetime to obtain a quantitative indexes of morphological change, administering the solutions to the organism specimen such as a cell, culturing the organism specimen, observing change of the organism specimen, and evaluating the compound solved in each solution. The quantitative indexes allow discrimination whether each compound is the candidate compound.

In this embodiment, the initial measurement before the dosage of each solution and the measurements at a predetermined interval after the dosage of the solution are performed. The morphological changes over time are detected and the screening of candidate compound is performed.

Figure 3A:
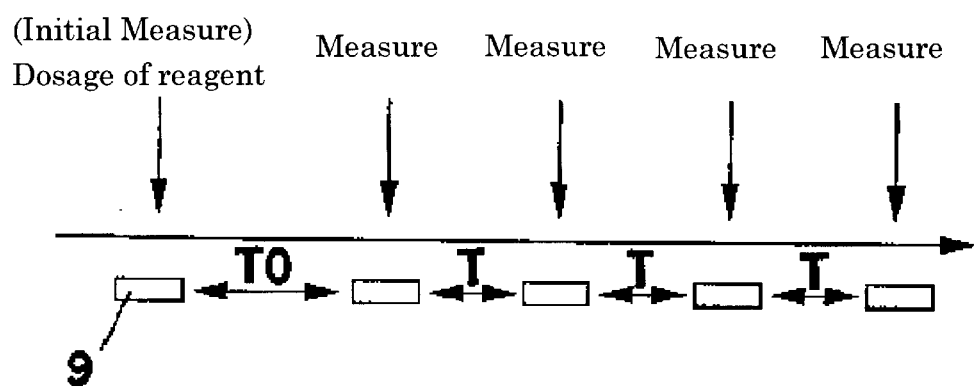
FIGS. 3A and 3B illustrate a candidate compound screening method in accordance with the exemplary embodiment.

Referring now to FIG. 3A, there are shown a timing of administering the solution to plate 9 storing the organism specimen and timings of sequential measurements by the taking of the microscopic image. First, initial measurement is performed before the dosage of the solution. Holding head 18 of plate conveying mechanism 14 takes plate 9 out of plate storing unit 22 for the initial measurement. Bar code reader 19 reads an identification number of the plate. The plate is identified by identifying unit 31 and then mounted onto XY stage 20a of microscope observing unit 20.

Next, XY stage 20a horizontally moves plate 9 to locate well 9a to be taken within a view field of camera 26. Camera 26 takes the microscopic image of the organism specimen in well 9a (image taking process before the dosage). At this time, positional data of XY stage 20a is obtained and stored. When the same specimen is again observed and taken image, its image taking position can be instantly reproduced. Image processor 32 processes the taken microscopic image to derive numeric data (numeric data before the dosage) that is a quantitative indexes of morphological change for indicating a state of the organism specimen in the microscopic image.

Figure 4A:
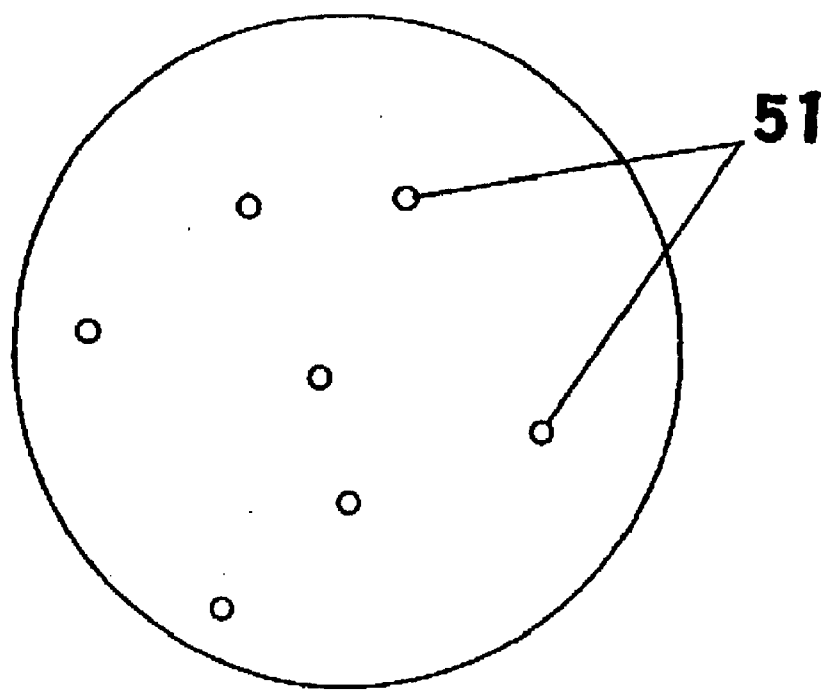
FIGS. 4A and 4B show microscopic images in the screening method illustrated in FIGS. 3A and 3B.
Figure 4B:
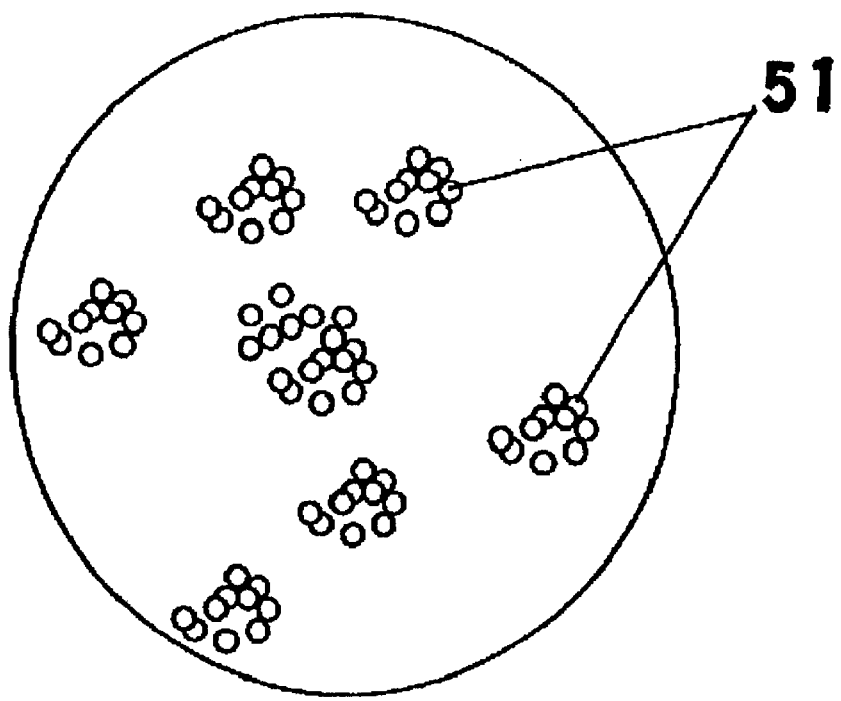
Figure 5A:
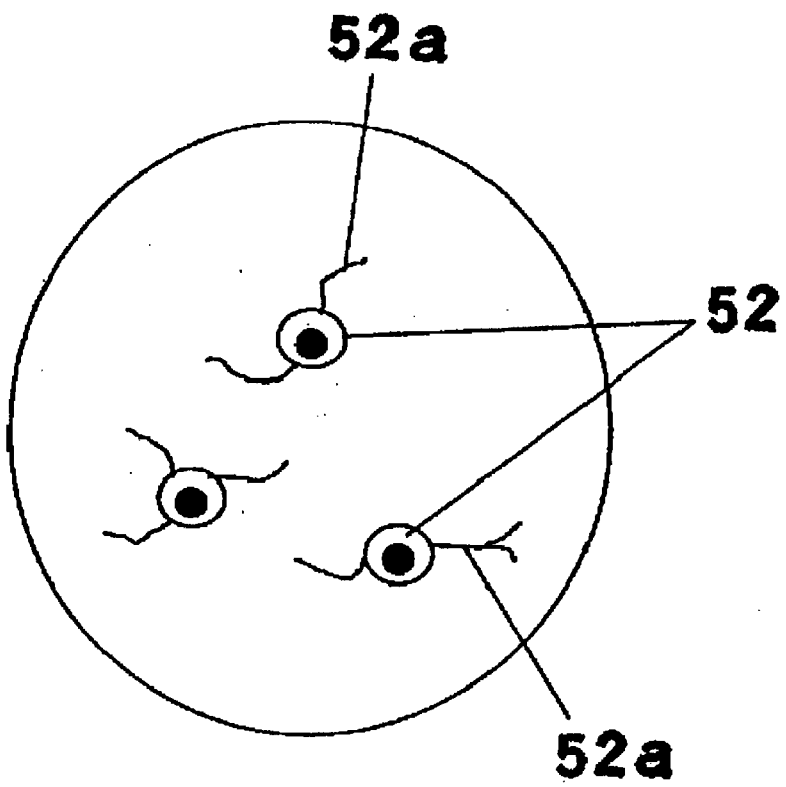
FIGS. 5A and 5B show microscopic images in the screening method illustrated in FIGS. 3A and 3B.
Figure 5B:
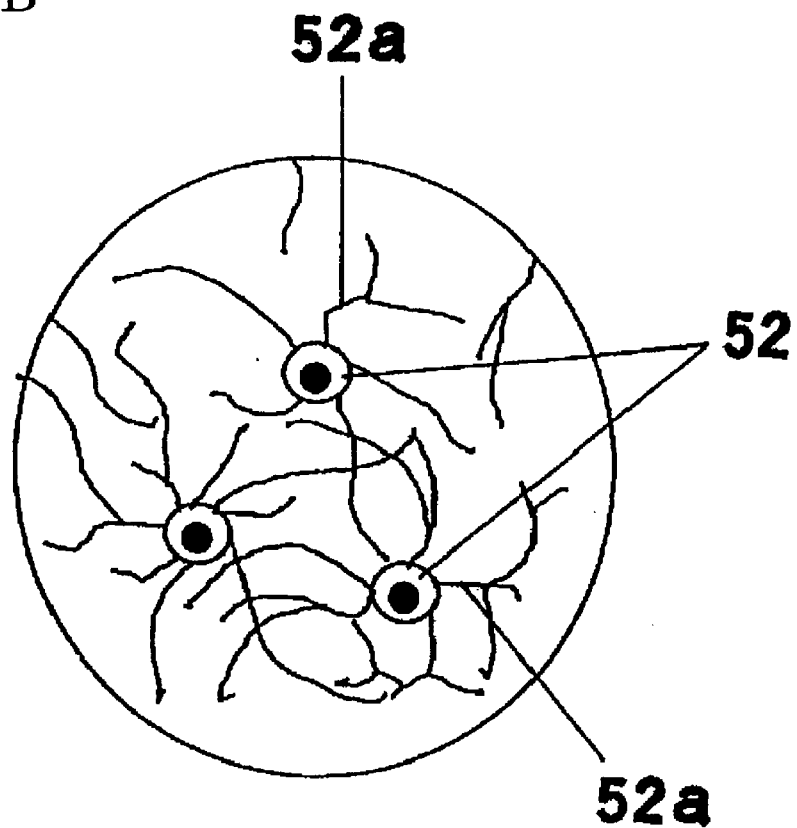

The obtained microscopic image and the quantitative indicator will be described. Referring now to FIG. 4A, FIG. 4B, FIG. 5A, and FIG. 5B, examples of microscopic images in well 9a are shown. FIG. 4A and FIG. 4B show images of observed division states of cells, and FIG. 5A and FIG. 5B show images of observed growth states of tree processes of cells. FIG. 4A and FIG. 5A show images in initial measurements before the dosage of the solutions, and FIG. 4B and FIG. 5B show microscopic images at a predetermined period incubation after the dosage of the solutions.

For obtaining quantitative indexes of morphological change from these images, a known image processing technology is applied. For example, the evaluation of the division state of cells 51 as shown in FIG. 4A and FIG. 4B can be performed using various quantitative indexes depending on observed objects in a following method:

(1) detecting groups (e.g. colonies) of cells 51 in the image, and obtaining total number and area of these groups as a quantitative indexes; or (2) obtaining total luminance as a quantitative index, when the cells can be detected simply based on difference of luminance on the image. In any case, the division state of cells can be objectively quantitatively evaluated based on numeric data.

While, the evaluation of tree processes 52a extending from cells 52 as shown in FIG. 5A and FIG. 5B can be performed using the following image processing method:

(1) searching tree processes 52a on the image, and obtaining numeric data such as total number of pixels equivalent to the length of a part corresponding to tree processes 52a; or (2) obtaining a quantitative index in a coding process of the image data.

Holding head 18 conveys measured plate 9 to dispensing stage 8, and dispensing head 12 administers a compound-containing solution.

Plate 9, after the dosage of the solutions, is mounted to a predetermined position in incubator 1. After a predetermined initial interval T0, plate 9 is taken out of incubator 1, identified, then mounted again onto XY stage 20a of microscope observation unit 20, and measured as discussed above. In this case, data in the initial measurement is read out from inspection result storing unit 40 on the basis of an identification number, and an image is taken under the same condition, namely at the same image taking position and scaling factor, as in the initial measurement. Numerical data for indicating the state of the organism specimen is obtained based on the taken microscopic image in a method similar to the initial measurement. Then, a measurement process comprising similar taking of the microscopic image and obtaining of the numerical data is repeated at continuous intervals T as shown in FIG. 3A. The numerical data is obtained after the dosage of the solution, and sequentially stored in inspection result storing unit 40 for every measurement. The post-dosage numerical data is obtained for every measurement, but the post-dosage numerical data to be compared for judging whether the compound dissolved in the solution is a candidate compound is adequately selected in response to an elapsed time after the dosage. The elapsed time is set responsive to the solution and/or a screening purpose. The post-dosage numerical data is compared with the pre-numerical data, and the comparison result is used to judge whether the compound is the candidate compound as described below.

At the initial interval between the dosage of the solution and first measurement after the dosage and subsequent continuous intervals, plate 9 is held in incubator 1 and incubated under a predetermined environmental condition. Initial interval T0 and continuous intervals T shown in FIG. 3A are arbitrarily set; all intervals may be same, or all intervals may be different from each other. Shorter initial interval T0 or continuous intervals T do not require conveying of plate 9 into incubator 1.

Figure 3B:
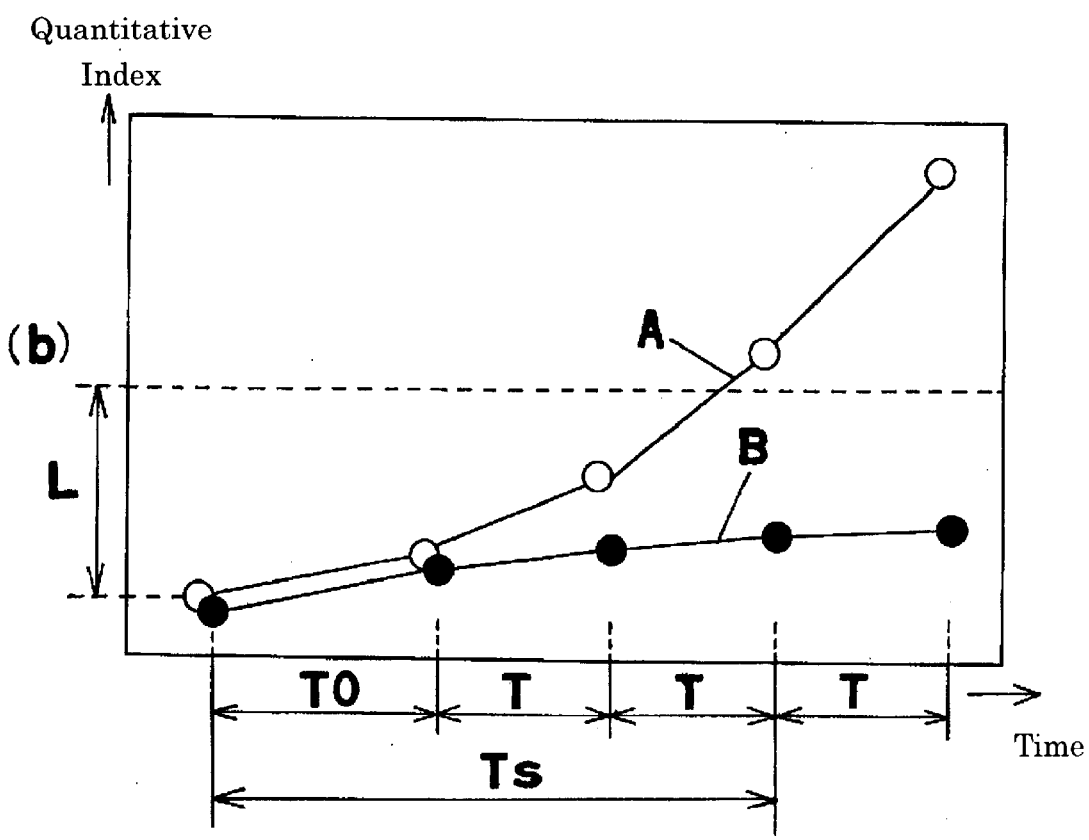

Screening unit 45 of candidate compound judges whether the compound solved in each solution is a candidate compound based on such obtained numerical data stored on inspection result storing unit 40. FIG. 3B shows morphological changes of observed organism specimens at intervals over time, and the morphological changes are used as reference data for discriminating a candidate compound. In FIG. 3B, the horizontal axis shows a lapse of time and the vertical axis shows measured numerical data, namely, quantitative index of the morphological changes.

Polygonal lines "A" and "B" show measurement results after different kinds of compound-containing solutions "a" and "b" are administered to the same kind of organism specimens and they are incubated under the same condition. The graphs are produced by processing the numerical data read by screening unit 45 with display processor 46, and displaying the processed data on a monitor of display unit 47.

When the morphological change of the organism specimen before and after the dosage of solution "a" is compared with the morphological change of the organism specimen before and after the dosage of solution "b", as understood in the graphs, difference between solution "a" and solution "b" is not so large just after the dosage. However, the graphs show that the morphological change for solution "a" noticeably increases with the passage of time. It is set, as a judgment reference, that if a morphological change value (difference between numerical data) is "L" or higher at elapsed time TS after the dosage, the compound solved in solution is judged as the candidate compound. Here, the morphological change value is derived by comparing numerical data of quantitative indicators before and after the dosage of the reagent with each other. Therefore, compound solved in solution "a" is judged as the candidate compound, and the compound solved in solution "b" is not determined as the candidate. A judgment condition of the candidate compound is not limited to this judgment reference. A judgment condition depending on a concerned medication action is previously registered in screening unit 45.

The graphs of the measurement results allow a user to visually judge the morphological change of the organism specimen. In other words, exact selection of the candidate compound is enabled based on objective judgment data. In this judgment, screening unit 45 may automatically judge the candidate compound based on the preset judgment reference and display it with the displayed graph, or a worker may judge referring to the graph.

For some organism specimen, among the numeric data after the dosage of the solution obtained above, numeric data just after the dosage is compared with the subsequent numeric data without initial measurement before the dosage of the solution, and the candidate compound is judged.

The plate after the dosage of the solution, in the screening, is held and cultured in incubator 1 under a predetermined environmental condition while the organism specimen is surviving. Measurement by the image taking is performed for the organism specimen during its lifetime. Accordingly, the morphological change of the same organism specimen with the passage of culturing time can be followed up, observed, and quantitatively data-processed.

Conventionally, an organism specimen can be observed and quantitatively data-processed only after the organism specimen has died in a visualization process such as a dyeing treatment. In the present invention, the observation and quantitative data processing can be followed up for the same live organism specimen. Information obtained in the new candidate compound screening can be thus improved quantitatively and qualitatively, and an operation accompanying the candidate component screening can be made efficiently.

In the present embodiment, the dispensing treatment for a dosage of the solution, the holding of the plate in an incubator, and the analysis and measurement using the image taking can be all performed in the same apparatus, and also the plate can be automatically conveyed among dispensing stage, microscope observation unit, and incubator. Therefore, a new candidate compound screening required a complex process can be efficiently performed.

Each function is performed in one biochemistry material treating apparatus of the present embodiment, but unit separately having each function may be integrated to assemble amorphological change detecting apparatus.

Additionally, the candidate compound detecting apparatus as an example of an organism-specimen morphological-change detecting system has been hitherto described, but this apparatus can be also applied for inspection or evaluation of various materials using organism-specimens.

In the present invention, during an observation of an organism specimen that is performed for the candidate compound screening and includes a dosage of a solution, a microscopic image of the organism specimen is taken and an image taking result is quantified as numerical data. Accordingly, a candidate compound can be selected efficiently and reliably.

What is claimed is:

1. An organism-specimen morphological-change detecting apparatus for detecting morphological change of an organism specimen, comprising:

a solution administering mechanism for administering a compound-containing solution to an organism specimen stored in a container disposed on a dispensing stage during a lifetime of the organism specimen;

a storing unit for storing an image-taking condition;

an image taking unit for taking (i) a microscopic image, under the stored image-taking condition, of the organism specimen at a first time before administering the compound-containing solution to the organism specimen, (ii) a second microscopic image, under the stored image-taking condition, of the organism specimen during the lifetime of the organism specimen at a second time which is after the administering of the compound-containing solution to the organism specimen, and (iii) a third microscopic image, under the stored-image taking condition, of the organism specimen during the lifetime of the organism specimen at a third time after the second time;

a quantitative evaluation unit for processing the first, second, and third microscopic images taken by said image taking unit and outputting first, second, and third numerical data, respectively, for indicating a state of the organism specimen; and an inspection result storing unit for storing the first, second, and third numerical data.

2. The organism-specimen morphological-change detecting apparatus according to claim 1, further comprising an incubator for storing under a predetermined environment the container after the administering of the compound-containing solution.

3. The organism-specimen morphological-change detecting apparatus according to claim 2, further comprising a conveying device for conveying the container among the dispensing stage, said image taking unit, and said incubator.

4. The organism-specimen morphological-change detecting apparatus according to claim 1, further comprising a candidate compound screening unit for;

comparing the first, second, and third numerical data with each other and judging whether or not compound included in the compound-containing solution is a candidate compound.

5. The organism-specimen morphological-change detecting apparatus according to claim 1, wherein said image taking unit is for taking microscopic images of the organism specimen at a predetermined interval after the administering of the compound-containing solution.

6. The organism-specimen morphological-change detecting apparatus according to claim 5, further comprising an incubator for storing under a predetermined environment the container after the administering of the compound-containing solution.

7. The organism-specimen morphological-change detecting apparatus according to claim 6, further comprising a conveying device for conveying the container among said solution administering mechanism, said image taking unit, and said incubator.

8. The organism-specimen morphological-change detecting apparatus according to claim 4, further comprising a morphological change evaluation unit for comparing with each other numerical data of the microscopic images.

9. The organism-specimen morphological-change detecting apparatus according to claim 5, wherein said image taking unit is for taking the microscopic images while the organism specimen is surviving.

10. The apparatus according to claim 1, wherein said storing unit is to store a scaling factor as the image taking condition.

11. The apparatus according to claim 1, wherein said storing unit is to store an image taking position of the organism specimen as the image taking condition.

12. The apparatus according to claims 11, wherein said storing unit is also to store a scaling factor as an image taking condition.

13. The apparatus according to claim 1, wherein the container has identification data attached thereto, said apparatus further comprising:

a reader for reading the identification data, wherein said inspection result storing unit is for storing the identification data and relating the first, second, and third numerical data to the identification data.

14. The apparatus according to claim 13, further comprising:

a clock for counting first and second elapsed times elapsing from a time when the compound-containing solution is administered to the organism specimen to the second and third times, respectively, wherein said inspection result storing unit is for storing the first and second elapsed times, relating the first elapsed time to the second numerical data and the identification data, and relating the second elapsed time to the third numerical data and the identification data.

15. The apparatus according to claim 1, further comprising:

a clock for counting first and second elapsed times elapsing from a time when the compound-containing solution is administered to the organism specimen to the second and third times, respectively, wherein said inspection result storing unit is for storing the first and second elapsed times, relating the first elapsed time to the second numerical data, and relating the second elapsed time to the third numerical data.

16. A method for detecting morphological change of an organism specimen stored in a container, comprising:

(a) administering a compound-containing solution to an organism specimen during a lifetime of said organism specimen;

(b) taking, a first microscopic image of said organism specimen at a first time before the administering of said compound-containing solution;

(c) deriving first numerical data, indicating a state of said organism specimen; by processing said first microscopic image, and storing said first numerical data;

(d) taking a second microscopic image of said organism specimen during the lifetime of said organism specimen at a second time which is after the administering of said compound-containing (e) deriving second numerical data indicating a state of said organism specimen by processing said second microscopic image, and storing said second numerical data;

(f) taking a third microscopic image of said organism specimen during the lifetime of said organism specimen at a third time which is after said second time;

(g) deriving third numerical data indicating a state of said organism specimen by processing said third microscopic image, and storing said third numerical data; and (h) comparing said first, second, and third numerical data with each other.

17. The method according to claim 16, further comprising maintaining said organism specimen, after the administering of said compound-containing solution, under a predetermined environment.

18. The method according to claim 16, further comprising judging whether or not a compound contained in said compound-containing solution is a candidate compound based on a result of comparing said first, second and third numerical data.

* * * * *

UNITED STATES PATENT AND TRADEMARK OFFICE
CERTIFICATE OF CORRECTION

PATENT NO. : 6,678,391 B2
DATED : January 13, 2004
INVENTOR(S) : Kanji Yahiro

It is certified that error appears in the above-identified patent and that said Letters Patent is hereby corrected as shown below:

<u>Title page,</u>
Item [57] ABSTRACT
Line 12, change "solved" to -- dissolved --.
Line 13, insert -- with each other -- after "comparing".
Line 14, delete "with each other" after "solution".

<u>Column 8,</u>
Line 7, insert -- first -- after "a".
Line 39, delete ";" after "for".
Line 41, insert -- a -- after "not".
Line 60, change "4" to -- 5 --.

<u>Column 10,</u>
Line 10, delete ";" after "specimen".
Line 15, insert -- solution; -- after "containing".

Signed and Sealed this

Twenty-seventh Day of April, 2004

JON W. DUDAS
*Acting Director of the United States Patent and Trademark Office*